United States Patent [19]
Trudell et al.

[11] Patent Number: 5,098,413
[45] Date of Patent: Mar. 24, 1992

[54] PERITONEAL CATHETER

[75] Inventors: Leonard A. Trudell, East Greenwich; Clarence J. Gdowski, Barrington, both of R.I.

[73] Assignee: Sil-Med Corporation, Taunton, Mass.

[21] Appl. No.: 549,976

[22] Filed: Jul. 9, 1990

Related U.S. Application Data

[63] Continuation-in-part of Ser. No. 322,190, Mar. 13, 1989, abandoned.

[51] Int. Cl.$^5$ ............................................. A61M 25/00
[52] U.S. Cl. ..................................... 604/281; 604/29; 604/175
[58] Field of Search ............... 604/29, 43, 93, 175, 604/264, 280, 281

[56] References Cited

U.S. PATENT DOCUMENTS

| 3,828,767 | 8/1974 | Spiroff | 128/658 |
| 4,488,877 | 12/1984 | Klein et al. | 604/175 |
| 4,557,724 | 12/1985 | Gregonis et al. | 604/49 |
| 4,687,471 | 8/1987 | Twardwoski et al. | 604/175 |
| 4,772,269 | 10/1988 | Twardowski et al. | 604/175 |
| 4,787,882 | 11/1988 | Clarén | 604/4 |
| 4,935,004 | 6/1990 | Cruz | 604/29 |

FOREIGN PATENT DOCUMENTS 0132344 1/1985 European Pat. Off. ............. 604/281

Primary Examiner—C. Fred Rosenbaum
Assistant Examiner—Anthony Gutowski
Attorney, Agent, or Firm—Barlow & Barlow, Ltd.

[57] ABSTRACT

A peritoneal catheter for introducing and withdrawing fluid from an abdominal cavity which catheter has a plurality of ingress and egress ports spaced about the circumference and along the length of the intra-abdominal portion, which ports are arranged to decrease in size from the proximal to the distal end and, further which has a body portion formed into at least a one-half turn. The catheter tubing and the ports therein are coated with Ultra-low Temperature Isotropic carbon.

6 Claims, 1 Drawing Sheet

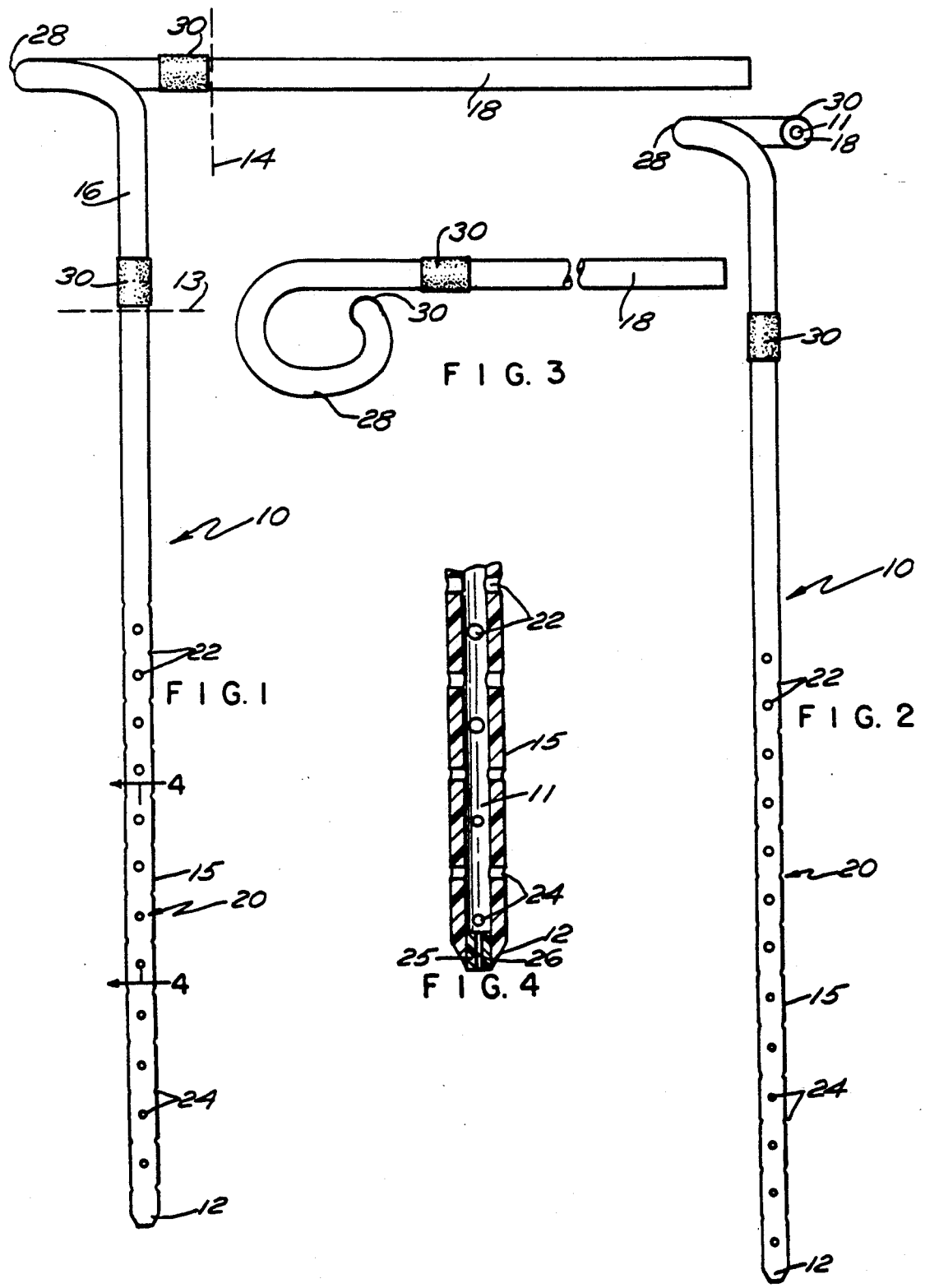

PERITONEAL CATHETER

CROSS-REFERENCE TO RELATED APPLICATION

This application is a continuation-in-part of our prior application Ser. No. 322,190, filed Mar. 13, 1989 (now abandoned).

BACKGROUND OF THE INVENTION

This invention resides in the field of catheters implantable within the human body and more particularly, relates to peritoneal catheters.

Peritoneal catheters are used in a method of treatment for kidney disease or failure known as peritoneal dialysis. The purpose of the treatment is the same as hemodialysis, that is, to remove the waste products or toxins from the blood by solute and fluid diffusion out of circulation. In hemodialysis, this is accomplished by circulating the blood outside the body through an artificial kidney in which toxins and excess fluids migrate through specific permselective membranes. In peritoneal dialysis, a solution or dialysate is introduced into the space between the abdominal wall and the thin membrane known as the peritoneum which covers the entire abdominal cavity and visceral organs. The peritoneum will act as a diffusion selective membrane for toxin removal when a proper dialysate is artificially placed in the above mentioned space. Once there, the fluid is allowed to dwell for a period of time, come to chemical equilibrium with circulating blood over several hours, and then the fluid is drained.

The cycle is repeated on a regular basis, the duration and frequency of which depends upon the patient's medical condition and the treatment regimen adopted. A catheter inserted into and extending outside the body is used for the introduction and removal of the dialysate.

A variety of peritoneal catheters exist in the prior art. Their design format is basically a flexible, straight or slightly bent tube having exit ports in the intra-abdominal portion and one or more unique design features. Such are described in *Peritoneal Dialysis Bulletin*, 1983 Vol. 3, No. 3, published by Peritoneal Dialysis Bulletin Inc., Toronto Western Hospital, Toronto, Ontario, Canada. These include cuffs or flanges which communicate with the walls of the body tunnel to block bacterial ingression (Tenckhoff); intra-abdominal immobilizers such as an inflatable balloon (Goldberg and Hill) or flanges (Toronto Western Hospital) to prevent catheter tip migration; and a dual columnar disc fluid distribution head positioned at the end of the intra-abdominal portion (Lifecath).

By way of background, United States Patents directed to or disclosing catheter devices include U.S. Pat. Nos. 1,626,839, Kallmeyer; 3,828,767, Spiroff; 4,173,981, Mortensen; 4,184,497, Kolff et al; 4,256,102, Monaco; 4,278,092, Borsanyi et al; 4,681,570, Dalton; and 4,687,471, Twardowski et al.

This invention disclosed herein is directed to the problem of limiting trauma to abdominal structures during dialysate introduction and to reducing the likelihood of blockage during fluid withdrawal. This may be accomplished by providing a generally flexible catheter arranged to introduce and withdraw dialysate in a smooth and uniform manner. The present invention functions to produce the above-desired result by providing in combination a catheter having a formed half helical turn arranged to be disposed within the body and a plurality of ports of decreasing size from the proximal to the distal end in the intra-abdominal portion in combination with an Ultra-low Temperature Isotropic carbon coating on the ports and the tubing.

This configuration, which consists of a structure not disclosed in the prior art known to the applicant, results in an even and wide spread distribution of fluid flow. The structure eliminates forceful streaming and catheter whip that is common in the prior art. The dialysate flowing through the bent portion of the catheter into the body undergoes a transformation from laminar flow to a spiral, rotary flow that has a radial component. Upon reaching the spatially distributed size graded ports in the intra-abdominal portion of the catheter, the fluid exits in a plurality of directions in what may be described as a gentle manner rather than with the strong directional force that will occur when either a single end port or series of in line ports are employed.

When the dialysate is removed after a dwell period, the same spacial and size graded configuration of ports results in an even, distributed withdrawal with a reduced likelihood of clogging, a problem which is of substantial concern in the use of many presently existing devices.

SUMMARY OF THE INVENTION

The invention may be summarized as a peritoneal catheter arranged to provide an evenly, distributed, low velocity ingress and egress of fluids to and from the abdominal cavity employing a plurality of radially and longitudinally positioned ports of graded diameter in the intra-abdominal portion and further having at least a one-half helical turn formed in the body portion. The flow characteristics are facilitated by longitudinal gradation of the port diameters, the small ports located at the intra-abdominal tip or the distal end and the largest nearest the body portion or the proximal end. The end port is similar in diameter to the adjacent side ports.

Dialysate entering the catheter during the initial stage of peritoneal dialysis is altered from a laminar flow to a spiral rotary flow that has a radial component after passing through the bent portion. As the fluid reaches the series of ports in the catheter's intra-abdominal portion, it is evenly distributed in a swirl about the interior of the tube and flows out of the catheter proportionally about its circumference.

This action continues down the length toward the tip where the additional distal port improves the flow characteristics. It has been observed that a further benefit is obtained by grading the ports such that the largest is away from the catheter tip. In this manner, the flow velocity is progressively reduced and more evenly distributed as the fluid travels to the end of the catheter.

Upon fluid withdrawal, the multiplicity of ports allows for an evenly distributed ingress into the catheter preventing any strong localized flow which would tend to draw the omentum against the wall of the tube. Additionally, the likelihood of clogging is reduced by the spacial distribution of the ports. Also from a clinical standpoint, even flow will reduce trauma in the patient.

The catheter is compatible with body tissue and is not encapsulated by oementum as a pure silicone rubber catheter would be by virtue of an Ultra-low Temperature Isotropic Carbon coating which substantially prevents the omentum, for example attempting to adhere to the catheter, which would substantially encapsulate the catheter and block the catheter holes.

The features and advantages of the invention will be more clearly understood from the description of the preferred embodiment and drawings which follow.

DESCRIPTION OF THE DRAWINGS

FIG. 1 is a side elevational view of the preferred embodiment of the invention;

FIG. 2 is an end view of the embodiment of FIG. 1;

FIG. 3 is a top view of the embodiment of FIG. 1 and;

FIG. 4 is a sectional view on lines 4—4 of FIG. 1;

DESCRIPTION OF THE PREFERRED EMBODIMENT

Referring first to FIG. 1, there is illustrated the catheter of the invention comprising a tube generally indicated 10 having a continuous bore 11 to the distal end 12. The catheter is divided into three segments namely an intra-abdominal portion 15 below line 13, a body portion 16 between lines 13 and 14, and an external body portion 18 above line 14. A plurality of ingress and egress ports 20 are located at the end of intra-abdominal portion 15 spaced about the circumference of tube 10. They are preferably graded longitudinally from the largest 22 to the smallest 24. The distal end 12 may also contain an additional port 26 indicated in FIG. 4 which is created by installing a plug 25 having a port no larger than 1.35 mm. in the distal end 12.

A one-half helical turn 28 is formed in body portion 16, the configuration of which is further shown by reference to top view FIG. 2. By the body portion what is meant is that portion of the catheter which will reside in the abdominal wall of the patient, i.e. the anatomical structure adjoining the peritoneum between the rectus muscle and the skin. It is essential that the body portion be formed with a helical turn in a fashion so that it will retain its shape after implantation in order that the function of the one-half turn be carried out. The helical, rotary motion imparted to the fluid by the helical half turn imparts an even distribution of the fluid over the many exit ports rather than allowing exit of the fluid through one dominant hole. This reduces the force of the fluid flow and consequently reduces the trauma inherent in running dialysis fluids into the abdominal cavity. Further it is equally important to drain the fluid with similarly little trauma that is accomplished by dividing the fluid reentrance into the catheter over a large area through many holes which limits the flow velocity in any one place.

Optionally and as is the practice with such catheters, one or two fibrous cuffs 30 composed of Dacron, for example, may be positioned over the body portion to seal the subcutaneous channel from bacteria by means of cellular ingrowth. The outer cuff is positioned so that it may be sutured to the subcutaneous tissue while the inner cuff is sutured to the posterior rectus sheath.

In accordance with the above disclosure, a catheter was constructed of silicone rubber or other suitable polymeric compound tubing having an inside diameter of 2.64 mm., an outside diameter of 4.87 mm. and an overall length of 47 cm.. The horizontal distance from the proximal end to the beginning of the turn (line 14) is 16 cm. and the vertical distance from that point to the distal end is 22-24 cm.

The vertical length of the turn is on the order of 1.3 cm. with an outside radius of 1.4 cm.. The distance from the end of the turn to the first port is 7.2 cm., after which 24 holes in four staggered rows of 6 each of a diameter of 1.12 mm. were placed a length of 7.0 cm.. These are followed by a similar series of 0.61 mm. holes spaced over approximately the same remaining length.

Tests utilizing dyed water gravity fed to the catheter immersed in clear water showed a thoroughly uniform dispersion pattern in accordance with the object of the invention. The invention shows even distribution of flow where the conventional prior art has essentially increased velocity and poorly distributed flow at the proximal and distal ends. Tests of conventional catheters and the invention illustrate interesting flow data. For example, a conventional catheter averages a discharge of 77.6 ml of fluid in 60 sec. while the invention discharges 82.8 ml in 60 sec. with a hydrostatic head of 13 cm. The invention shows, therefore an average of 6.7% better inflow and better outflow than the control unit of the prior art.

Clinical studies on humans have been conducted and the catheter has performed perfectly for periods of nine up to eighteen months and clinically, significantly better inflow and outflow has been noted but measurement data was not recorded. These results are to be compared to average implant time for standard catheters of eight months. The longevity of the implant indicates that there was no attachment by the omentum to the catheter of the invention.

The catheter is preferably composed of silicone elastomer coated with Ultra-low Temperature Isotropic (ULTI) carbon, or another non-reactive material, which serves to round the edges of the ports and coat the ports which reduces or eliminates body reaction to the entire device. The particular coating which in essence is applied in molecular layers to the surface of the catheter is an important element of the catheter. Carbon coatings are generally applied by a sputtering or vacuum vapor process at elevated temperature that is not possible with a silicone rubber catheter. The ULTI carbon coating is achieved by a hybrid low pressure process where isotropic carbon can be deposited from a gaseous precursor at ambient temperatures by using a proprietary catalyst and is successful on devices having a certain degree of flexibility and a low melting point.

It will be apparent from the foregoing that the advance in the catheter is the curved component section coupled with graduated diameter holes and the coating with ultra-low temperature isotropic carbon. The curve imparts centrifugal motion to the fluid flowing in which allows the fluid stream to exit the catheter through all the holes rather than through only a few or one end hole. The distribution of holes also avoids pulling abdominal structures into the flow path and drainage can proceed without obstruction.

The method of use and improved and advantageous operation of the apparatus are as described above. Variations of the device disclosed herein may occur to those skilled in the art. Accordingly, the invention is defined by the following claims.

We claim:

1. A peritoneal catheter for introducing into and withdrawing fluid from an abdominal cavity comprising a length of tubing having an intra-abdominal portion, a body portion, and an external body portion, said intra-abdominal portion having a distal end port and further having a plurality of ingress and egress ports positioned about its circumference and along its length, said ingress and egress ports of graded diameter, the smallest positioned closest to said distal end port and the largest positioned closest to said body portion, said distal end port having a diameter less than the inner diameter of said tubing, said body portion formed into at least a one-half helical turn a selected distance above the position of said ports that transform the flow into a flow with a radial component.

2. The apparatus of claim 1 wherein at least the intra-abdominal portion has a coating thereon of ultra low temperature isotropic carbon.

3. The apparatus of claim 1 wherein the helical turn has a diameter on the order of 2.8 cm.

4. The apparatus of claim 1 wherein the pitch of the helical turn is on the order of 1.3 cm.

5. The apparatus of claim 1 wherein the catheter is formed from silicone rubber.

6. The apparatus of claim 1 wherein the catheter is formed of polymeric material.

* * * * *